United States Patent

Giraud et al.

[11] Patent Number: 5,925,797
[45] Date of Patent: Jul. 20, 1999

[54] β-METHYLENE ALDEHYDES AND PREPARATION OF COMPOUNDS OF INTEREST BY MEANS OF THE β-METHYL ALDEHYDES

[75] Inventors: Michel Giraud, Estampes; Pierre Potier, Paris; Zo Andriamialisoa, Les Ulis; Alain Valla, Drancy, all of France

[73] Assignee: Centre National de la Recherche Scientifique (CNRS), Paris Cedex, France

[21] Appl. No.: 08/647,109

[22] Filed: May 9, 1996

[51] Int. Cl.$^6$ ............... C07C 45/00; C07C 47/02
[52] U.S. Cl. ............... 568/446; 568/447; 568/448
[58] Field of Search ............... 568/446, 447, 568/448

[56] References Cited

FOREIGN PATENT DOCUMENTS

| 731160 | 3/1966 | Canada . |
| 1243824 | 9/1960 | France . |
| 678424 | 9/1991 | Switzerland . |

OTHER PUBLICATIONS

Huche, 3,3 Sigmatrophic Cope–Claisen Rearrangement, Tetrahedron Lett., 30, 2607–10 1976.
Cresson, Vinylation of allenic alcohols, C.R. Hebd. Seances Acad. Sci., Ser. C, 279(20), 859–61 1974.
Abstracts only.

*Primary Examiner*—José G. Dees
*Assistant Examiner*—Alton Pryor
*Attorney, Agent, or Firm*—Jacobson, Price, Holman & Stern, PLLC

[57] ABSTRACT

The invention relates to the β-methylene aldehydes of formula:

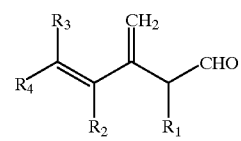

in which:

$R_1$ and $R_2$, which may be identical or different, are chosen from a hydrogen atom and optionally substituted carboacyclic, radicals, $R_3$ and $R_4$, which may be identical or different, are chosen from a hydrogen atom and optionally substituted carbocyclic, radicals, it not being possible for $R_3$ and $R_4$ simultaneously to be a hydrogen atom.

The invention also relates to the use of these compounds for the preparation of compounds of interest, in particular from the retinoid or carotenoid family, and the respective structural analogs thereof.

16 Claims, No Drawings

β-METHYLENE ALDEHYDES AND PREPARATION OF COMPOUNDS OF INTEREST BY MEANS OF THE β-METHYL ALDEHYDES

The invention relates to novel β-methylene aldehydes which are useful in the preparation of compounds of interest, in particular retinoid or carotenoid derivatives and the respective analogs thereof.

The invention also relates to the use of β-methylene aldehydes as intermediates in the synthesis of said compounds of interest and to a process for the preparation of said compounds of interest by means of the abovementioned β-methylene aldehydes.

Lastly, the invention relates to a process for the preparation of β-methylene aldehydes and to novel compounds which are useful in particular in said preparation process.

Much research has already been devoted to the synthesis and biological properties of vitamin A, of retinal, of retinoic acid, of retinoids and of carotenoids and also to the respective structural analogs of these biological molecules.

The synthesis of these biological molecules requires the reactions to be carried out according to a determined stereospecificity, given the E or Z structures of the ethylenic double bonds present along said molecules.

The structures of four well-known retinoic acids will be recalled below:

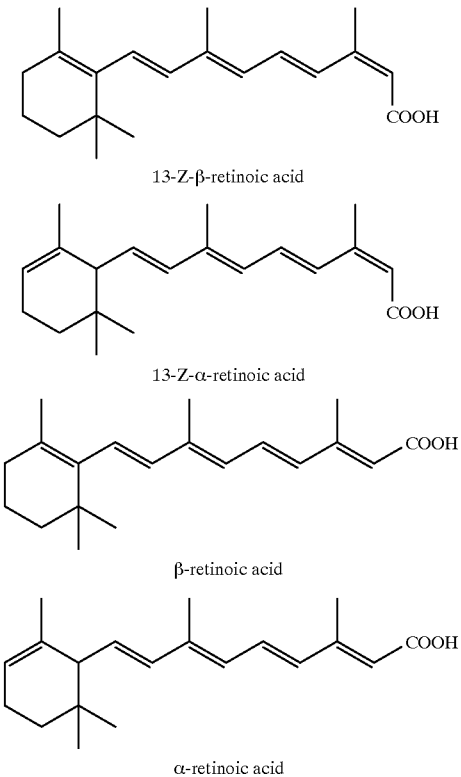

All these derivatives may be used in fields as varied as human therapy, cosmetology or the agri-foods industry.

In the case of human therapy, these derivatives are useful in the treatment of psoriasis and severe acnes and it would furthermore seem that certain retinoids may be useful in the field of combating cancer.

One of the main methods of synthesis for accessing these various compounds is described in French patent 1,243,824 and consists in using as starting material substituted acetaldehydes of E configuration, such as 9 E α- and β-ionylideneacetaldehydes whose general structure is represented in the formula below in which $R_4$ is a 2,6,6-trimethylcyclohexene group:

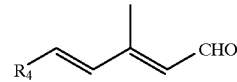

The condensation of these 9 E-α- and -β-ionylideneacetaldehyde compounds with a compound containing activated hydrogen such as, for example, an alkylisopropylidenemalonate followed by a partial decarboxylation leads in particular to retinoic acids as mentioned above.

Nevertheless, the use of 9 E-α- and -β-ionylideneacetaldehydes has certain difficulties owing to the fact that these compounds have a set 9 E configuration and, consequently, the yield of the preparation process is relatively low since it requires a purification step in order to remove the 9 Z-α- and -β-ionylideneacetaldehydes.

Besides this purification step, the synthetic routes to these compounds involve reactions and reagents which are dangerous and difficult to use on a large scale.

It is thus desirable to find other synthetic intermediates which allow these drawbacks to be overcome.

The authors of the present invention have found novel compounds whose condensation with compounds containing activated hydrogen lead to the same products as those obtained from 9 E-α- and -β-ionylideneacetaldehydes, that is to say with the same stereospecificity.

Moreover, these compounds possess no set configuration of 9 E or 9 Z type and may consequently be obtained in excellent yields, on a large scale, for very reasonable costs.

Moreover, these compounds open the way to a process for the preparation of compounds of interest in excellent yields and under mild conditions which avoid, in particular, the use of strong bases such as sodium amide which are usually used in condensations with compounds containing activated hydrogen.

The α- and β-methylene aldehydes according to the invention correspond to the formula:

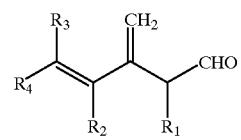

in which:

$R_1$ and $R_2$, which may be identical or different, are chosen from a hydrogen atom and optionally substituted carboacyclic, carbocyclic or heterocyclic radicals.

$R_3$ and $R_4$, which may be identical or different, are chosen from a hydrogen atom and optionally substituted carbocyclic, carboacyclic or heterocyclic radicals, it not being possible for $R_3$ and $R_4$ simultaneously to be a hydrogen atom.

A carboacyclic group is a linear or branched carbon chain optionally containing one or more ethylenic or acetylenic unsaturations. The carboacyclic radicals may optionally be substituted. The carboacyclic groups generally contain between 1 and 12 carbon atoms and 0 to 5 ethylenic or acetylenic unsaturations.

In general, a carbocyclic or heterocyclic group is a saturated or unsaturated, aromatic or nonaromatic monocyclic system, a saturated or unsaturated, aromatic or nonaromatic polycyclic system or a saturated or unsaturated bridged system. These groups may optionally be substituted.

The hetero atoms forming part of the heterocycles are chosen from nitrogen, oxygen, phosphorus and sulfur atoms.

The radicals $R_1$ to $R_4$ may have one or more asymmetric centers and thus make the compounds of formula (I) optically active.

The substituents (Z) which may be allowed are any substituent which does not interfere with the reaction involving the aldehyde function, in particular the reaction of this aldehyde function with the activated hydrogen of a reactant.

The number of substituents (Z) must not be such that these substituents constitute an excessive steric hindrance liable to make the molecule unstable or too difficult to access.

In the case of carbocyclic, carboacyclic or heterocyclic groups, the substituents (Z) which may be allowed are identical or different and are chosen from halogen atoms (I, Cl, Br and F), alkyl, haloalkyl, hydroxyl, alkoxy, haloalkoxy, thiol, alkylthio, halo-alkylthio, alkylsulfinyl, haloalkylsulfinyl, alkyl-sulfonyl, haloalkylsulfonyl, alkoxycarbonyl, haloalkoxy-carbonyl, alkylcarbonyloxy, haloalkylcarbonyloxy, alkyl-carbonyl, haloalkylcarbonyl, amino, alkylamino, halo-alkylamino, dialkylamino, dihaloalkylamino, alkylhalo-alkylamino, nitro, cyano, oxo, optionally cyclic acetal, imine, oxime and carboxyamido radicals and a residue —S(O)$_m$—R in which R is an amino, alkylamino or dialkyl-amino group and m=0, 1 or 2.

The prefix alkyl mainly covers linear or branched alkyl residues of 1 to 12 carbon atoms, advantageously of 1 to 6 carbon atoms.

The prefix halo means mono- or polyhalo. The number of substituents (Z) is generally between 1 and 6.

Preferably, the monocyclic systems may be represented by the formula:

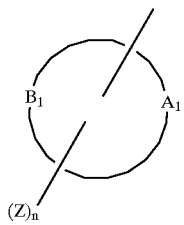

in which $B_1$ represents a saturated or unsaturated carbon and $A_1$ represents a chain of atoms which, together with $B_1$, forms a monocyclic system containing from 0 to 3 double bonds. $A_1$ may comprise 2 to 7 carbon atoms or may comprise a combination of 2 to 6 carbon atoms and 1 to 3 hetero atoms which may be chosen independently from N, O, S and P or another hetero atom.

The systems comprising hetero atoms may, in certain cases, bear oxygen atoms, for instance in aromatic systems containing an N-oxide group or containing a sulfinyl, sulfonyl, selenoxide or phosphine oxide group.

Certain carbons of the rings formed by $A_1$ and $B_1$ may carry carbonyl, thiocarbonyl, methylidene, oxime or imino groups optionally substituted with a $C_{1-C6}$ alkyl, $C_{3-C8}$ cycloalkyl or $C_{6-C10}$ aryl group, said groups optionally being substituted with 1 to 6 groups (Z) as defined above.

The group denoted by (Z) represents one or more substituents chosen independently from the group of substituents defined above for (Z). In general, n=0 to 6.

Among the bicyclic systems which may be mentioned are aromatic systems such as naphthalene, benzimidazole, biphenyl, indene, azulene, and the like.

Among the tricyclic systems which may be mentioned are aromatic systems such as anthracene, phenanthrene, fluorene, indacene, acenaphthene, and the like.

Among the bridged systems which may be mentioned are norbornane, pinene, camphene, bicyclo[3.2.1]octane, and the like.

According to a preferred variant, the radicals $R_3$ and $R_4$ are chosen from carbocyclic or heterocyclic radicals.

According to a preferred variant, one of the radicals $R_3$ and $R_4$ is a hydrocarbon radical and the other radical is a hydrogen atom.

According to another preferred variant taken in combination with the previous one, $R_4$ is a hydrocarbon radical.

Preferably, $R_4$ is an optionally substituted mono- or di-unsaturated aromatic ring containing 6 carbon atoms.

Preferably, the substituents are chosen from $C_{1-C4}$ alkyl, hydroxyl, $C_1$–$C_4$-alkoxy and oxo radicals.

Preferably also, $R_2$ is a hydrogen atom.

According to another preferred variant, $R_1$ is a hydrogen atom.

According to a preferred variant, the unit:

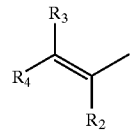

is a terminal residue of a compound chosen from biological molecules such as retinoids, carotenoids and the respective structural analogs thereof.

Among these compounds which may be mentioned are the derivatives whose formulae are as follows:

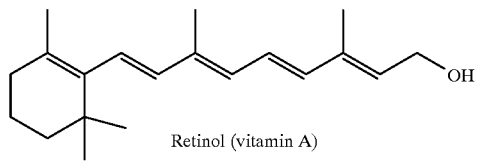

Retinol (vitamin A)

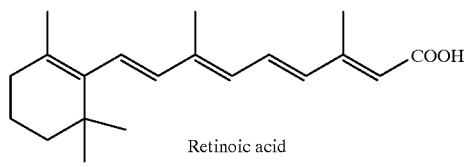

Retinoic acid

-continued
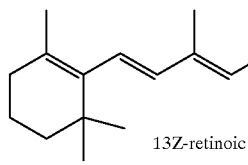
13Z-retinoic acid
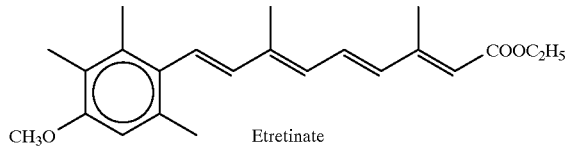
Etretinate
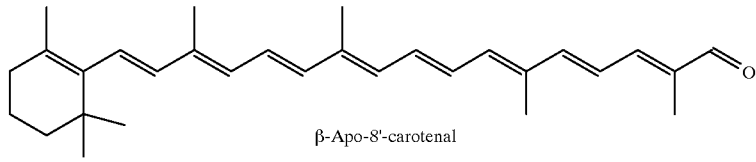
β-Apo-8'-carotenal
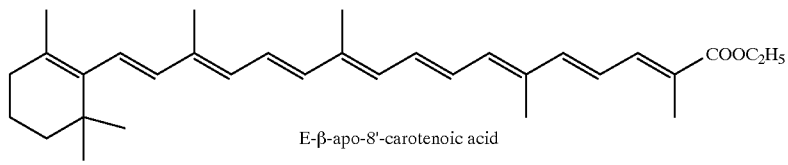
E-β-apo-8'-carotenoic acid
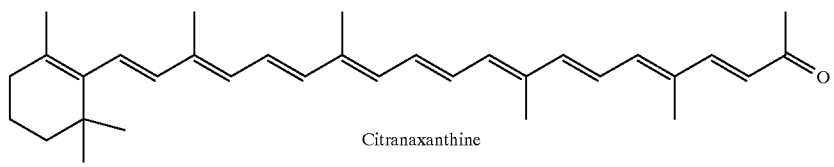
Citranaxanthine
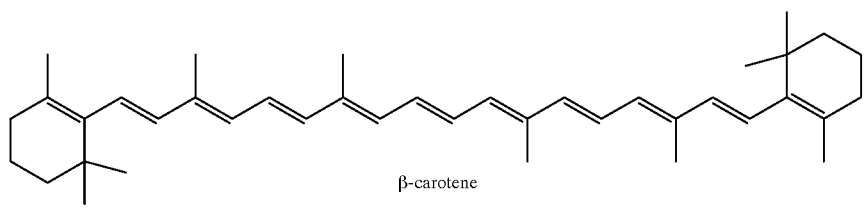
β-carotene
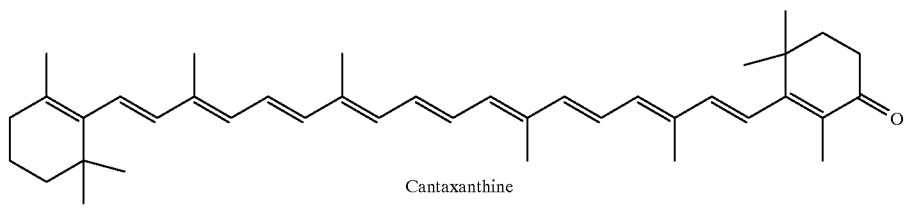
Cantaxanthine
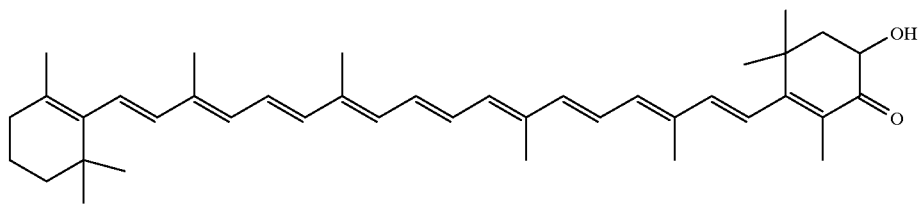
Astaxanthine
Preferably, $R_4$ is a cyclohexenyl radical substituted in positions 2, 6 and 6 with methyl radicals and corresponds to the formulae:

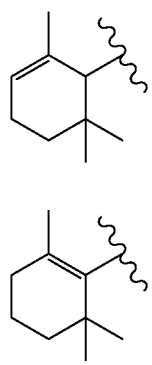

α

β

The invention also relates to a process for the preparation of compounds of interest, wherein a compound of formula (I) as defined above is reacted with a compound having a hydrogen capable of being activated, of formula (II), according to the following reaction:

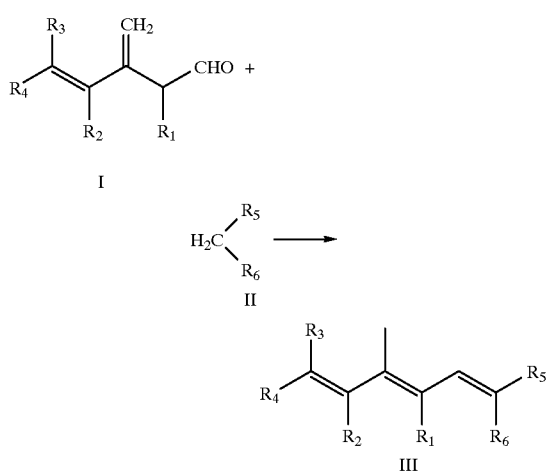

$R_1$, $R_2$, $R_3$ and $R_4$ have one of the meanings indicated above and $R_5$ and $R_6$, which may be identical or different, are a hydrogen atom, a lower alkyl radical or an electron-withdrawing group on condition that one of the radicals is an electron-withdrawing group, or $R_5$ is a hydrogen atom and $R_6$ is a group —$CR_7$=$C(R_8)_2$ where $R_7$ is a hydrogen atom or a lower alkyl radical, an alkylsulfonyl or arylsulfonyl radical and $R_8$ is an electron-withdrawing group.

The electron-withdrawing groups are well known and are chosen in particular from ester, cyano, carboxylic, alkylsulfonyl and arylsulfonyl groups.

The term "activated hydrogen" is generally understood to refer to a hydrogen atom located on an activated methylene or a vinylogously activated methyl.

The reaction is carried out in the presence of an agent which activates said hydrogen. The reaction may be carried out in basic medium, in particular in the presence of an alkaline amide. However, and this is one of the additional advantages of the present invention, the reaction may be carried out under mild conditions in the presence of a quaternary ammonium hydroxide such as Triton B or an equivalent base.

A compound of formula III is recovered,

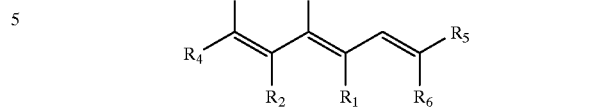

which compound is optionally converted.

Preferably, as has already been mentioned previously, the compound of formula II is involved in the skeleton of a compound chosen from retinoids, carotenoids and the respective structural analogs thereof as are presented, for example, in the formulae of these compounds mentioned above.

Preferably, the compound of formula II corresponds to the formula

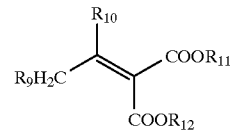

in which:

$R_9$ is a hydrogen atom or an optionally substituted alkyl radical, in particular methyl, $R_{10}$ is a hydrogen atom or an alkyl radical, $R_{11}$ and $R_{12}$ are such that the ester functions $COOR_{11}$ or $COOR_{12}$ can be hydrolyzed into acid functions and the compound of formula III corresponds to the formula:

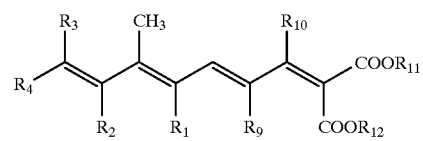

According to a preferred variant, the I/II molar ratio is between 0.2 and 2. Preferably also, the compound of formula II is an isopropylidenemalonic acid diester. Among the diesters which may be mentioned are $C_{1-C4}$ diesters, such as the methyl or ethyl ester.

According to a variant, the compound of formula III is hydrolyzed into a compound of formula IV

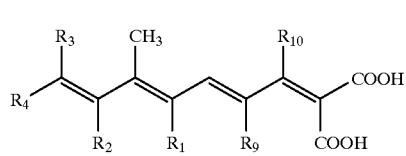

the latter compound being subsequently decarboxylated in order to obtain the compound of formula V

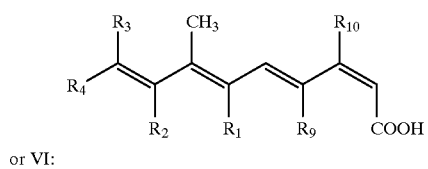

V or VI:

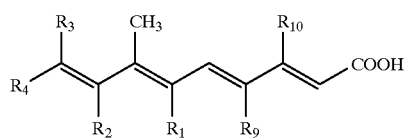

VI

The hydrolysis and decarboxylation reaction is carried out in a known manner.

The conversion of the acids of formula V and VI into corresponding alcohol or aldehyde is performed in a known manner.

The subject of the invention is also a process for the preparation of compounds of formula I.

In this process, an ethylenic ketone of formula:

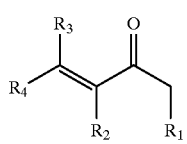

VII is reacted with a formate of formula $HCOOR_{13}$ $R_{13}$ being in particular a linear or branched alkyl residue, in order to obtain the compound of formula:

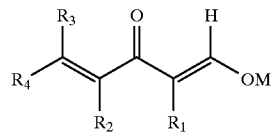

VIII

M is an alkaline metal or a hydrogen atom.

This reaction is generally carried out in the presence of a base such as alkaline alkoxides, alkaline hydrides, alkaline amides, etc., in a polar or apolar aprotic solvent such as cyclic or acyclic saturated hydrocarbons, for instance hexane and cyclohexane, aromatic hydrocarbons, for instance toluene and xylene, ethers, for instance ethyl ether and tetrahydrofuran, and the like.

The compound of formula VIII is subsequently acetalized to a compound of formula:

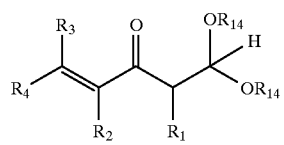

IX the radicals $R_{14}$ being in particular linear or branched alkyl radicals or represent a ring such as $(CH_2)_n$, with n =1, 2, 3 or 4. The acetalization reaction is carried out in a known manner.

By methylenation of the ketone function, in particular by means of the Wittig reaction, a methyltriphenylphosphonium or methyltrialkylphosphonium halide is reacted in order to obtain the β-methylene acetal of formula X

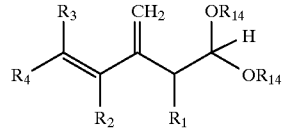

X

The β-methylene acetal X is then hydrolyzed to give the β-methylene aldehyde of formula I.

The subject of the invention is also the novel compounds of formulae VIII, IX and X which are useful in particular in the preparation of the compounds of formula I.

The invention is now illustrated by the examples which follow, which are given as a guide.

EXAMPLE 1

Preparation of the compound of formula

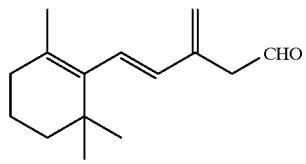

Synthetic scheme

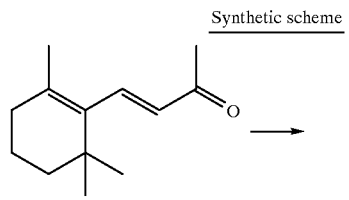

1

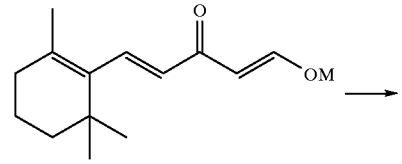

2

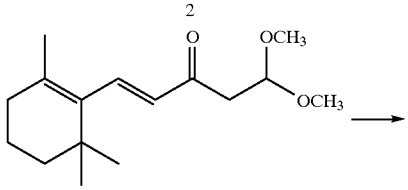

3

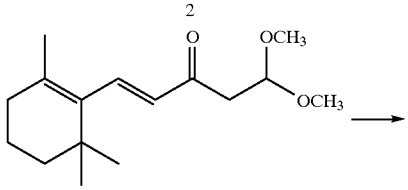

4

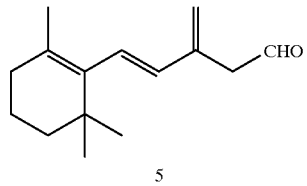

a) Preparation of compound No. 2 (sodium salt)

A mixture of 192 g (1 mol) of β-ionone and 120 g (2 mol) of methyl formate (employed in excess on account of its volatility) are added, at about 10° C. and over 15 min, to a suspension of 64.8 g (1.2 mol) of sodium methoxide in 200 ml of anhydrous cyclohexane. The mixture is allowed to return to room temperature (about 30 min), filtered and the sodium salt is washed with cyclohexane. Off-white beige powder. Yield ≧90%.

Compound No. 2 in which M=H is prepared by acidification of the sodium salt at 0° C. by 10% HCl solution. The product is rapidly extracted with ether, washed with water, dried and stored in the cold.

b) 1—Preparation of compound No. 3

10 ml of acetyl chloride are added, dropwise at about 10° C., to 30 g of sodium salt in suspension in 100 ml of anhydrous methanol and 30 ml of methyl formate. After stirring for 30 min, the mixture is neutralized slowly with sodium bicarbonate. It is filtered and the precipitate is washed with cyclohexane. The methanol and cyclohexane are distilled off under reduced pressure (yield ≧85%). The product requires no purification for the following step (analytically pure sample obtained by chromatography on a column of silica (pentane/ether, 60v-40v).

b) 2—Preparation of compound No. 3

According to the same principle as b) 1, but with anhydrous isopropanol, the expected compound is obtained (yield ≧75%).

c) Preparation of compound No. 4

7.2 g (20 mmol) of $CH_3P\Phi_3$ (methyltriphenylphosphonium bromide) are added by spatula, under argon and over 10 min, to 15 ml of n-butyllithium (1.6 M, 30 mmol in hexanes) in 30 ml of anhydrous ether. After stirring for 4 h at room temperature, the mixture is cooled to 0° C. and 11.5 g of dimethyl β-keto acetal in solution in 30 ml of anhydrous ether are added slowly (15 min). After stirring for 2 h at room temperature, the mixture is cooled to about 0° C. and is hydrolyzed with ammonium chloride solution. The mixture is filtered and the gummy residues are washed with pentane. The organic phases are combined, filtered and the oil obtained after distillation of the solvents under reduced pressure is purified by chromatography on a column of silica (pentane/ether, 90v/10v). Yield =40%.

It is possible to improve this synthesis in the following way:

35.7 g (0.1 mol) of $CH_3P\Phi_3$ are added over 15 min to 11.2 g (0.1 mol) of tert-BuOK in 100 ml of anhydrous cyclohexane. The mixture is heated at 45° C. for 15 min and is then cooled to about 10° C. 26.6 g (0.1 mol) of β-keto-acetal in 50 ml of anhydrous cyclohexane are then added slowly. After 15 min at room temperature, the solvent is distilled off under reduced pressure and the dimethyl β-methylene acetal is adsorbed on 150 g of silica and eluted with 1 l of methylene chloride. Yield ≧80%.

d) Preparation of compound No. 5

10 g of acetal in 40 ml of cyclohexane and 15 ml of formic acid are stirred for about 4h at room temperature. 40 g of ice are added, the phases are separated by settling and the aqueous phase is washed with cyclo-hexane. The organic phases are combined and washed with sodium bicarbonate solution and then with water until the washing waters are neutral. Very pale yellow oil. Yield ≧95%.

The overall yield for the reaction (going from compound 1 to compound 5) is ≧72.5%.

The characteristics of the compounds 2, 3, 4 and 5 obtained are given below.

compound No. 2 (sodium salt) IR (KBr) 2940, 2865, 1644, 1597, 1500, 1450, 1345, 1170, 980, 770, 565. $^1$H NMR ($D_2O$): 0.88 (s, 6H, $C_6$—$CH_3$); 1.35 (m, 2H, $C_5$—H); 1.65 (m, 2H, $C_4$—H); 1.77 (a, 3H, $C_2$-$CH_3$); 1.87 (m, 2H, $C_3$—H); 5.20 (d, 1H, J=12, $C_{10}$—H); 6.10 (m, 1H, $C_8$—H); 6.85 (d, 1H, J=16, $C_7$—H); 8.95 (d, 1H, J=12, $C_{11}$—H).

compound No. 2 IR 2960, 2930, 2870, 1610, 1470, 1300, 980, 770, 565. $^1$H NMR ($CDCl_3$); 1.00 (B, 6H, $C_6$—$CH_3$); 1.49 (m, 2H, $C_5$—H); 1.58 (m, 2H, $C_4$—H); 1.71 (s, 3H, $C_2$-$CH_3$); 2.00 (m, 2H, $C_3$—H); 5.51 (d, 1H, J=3.5, $C_{10}$—H); 5.86 (d, 1H, J=16, $C_7$—H); 7.33 (d, 1H, J=16, $C_8$—H); 8.44 (d, 1H, J=3.5, $C_{11}$—H).

compound No. 3 IR (Film vcm$^{-1}$) 2935, 2875, 2830, 1697, 1664, 1610, 1465, 1370, 1320, 1130, 1080, 980. $^1$H NMR ($CDCl_3$): 1.09 (s, 6H, $C_6$—$CH_3$); 1.40 (m, 2H, $C_5$—H); 1.75 (m, 2H, $C_4$—H); 1.79 (3H, $C_2$—$CH_3$); 2.08 (m, 2H, $C_3$—H); 2.92 (d, 2H, J=5.5, $C_{10}$—H); 3.41 (s, 6H, $OCH_3$); 4.38 (t, 1H, J=5.5, $C_{11}$—H); 6.18 (d, 1H, J=16, $C_7$—H); 7.28 (d, 1H, J=16, $C_6$—H). $^{13}$C NMR ($CDCl_3$): 18.7 ($C_4$); 21.8 ($C_6$—$CH_3$); 28.8 ($C_2$-$CH_3$); 33.6 ($C_3$); 33.9 ($C_6$); 39.8 ($C_5$); 44.2 ($C_{10}$); 54.0 ($OCH_3$); 102.3 ($C_{11}$); 130.9 ($C_7$); 136.1 ($C_2$); 136.6 ($C_1$); 143.2 ($C_8$); 196.5 ($C_9$).

analog of compound No. 3 (isopropyl acetal) IR (film): 2970, 2932, 1692, 1665, 1607. $^1$H NMR ($CDCl_3$): 1.04 (s, 6H, $C_6$—$CH_3$); 1.1 and 1.16 (2d, 12H, J=7, $OCH(CH_3)_2$; 1.46 (m, 2H, $C_5$—H); 1.60 (m, 2H, $C_4$—H); 1.74 (s, 3H, $C_2$—$CH_3$); 2.04 (m, 2H, $C_3$—H); 2.84 (d, 2H, J=5.5, $C_{10}$—H); 3.84 (m, 1H, $C_{12}$—H); 5.0 (t, 1H, J=7, $C_{11}$—H); 6.12 (d, J=16, $C_8$—H); 7.28 (d, 1H, $C_7$—H).

compound No. 4 IR (film): 2930, 1602, 1122, 1068, 971, 888. $^1$H NMR ($CDCl_3$); 6.13 and 5.99 (2d, 2H, J=16, $C_7$—H+$C_8$—H); 5.02 and 4.99 (2 bs, 2H, $C_9$—H); 4.56 (t, 1H, J=5.5, $C_{11}$—H); 3.32 (s, 6H, $OCH_3$); 2.55 (d, 2H, J=5.5, $C_{10}$—H); 1.96 (m, 2H, $C_4$—H); 1.65 (s, 3H, $C_2$—$CH_3$); 1.59 (m, 2H, $C_5$—H); 1.42 (m, 2H, $C_4$—H); 0.97 (s, 6H, $C_6$—$CH_3$). $^{13}$C NMR ($CDCl_3$): 141.7 ($C_1$); 137.6 ($C_2$); 135.1 ($C_7$); 129.2 ($C_9$); 127.6 ($C_8$); 116.5 ($CH_2$—$C_9$); 103.7 ($C_{11}$); 53.3 ($OCH_3$); 39.5 ($C_{10}$); 36.1 ($C_5$); 34.3 ($C_6$); 32.9 ($C_3$); 29.0 ($C_2$-$CH_3$); 21.7 ($C_6$—$CH_3$); 19.4 (C-4).

compound No. 5 IR (film): 2930, 2715, 1727, 1603. $^1$H NMR ($CDCl_3$): 9.60 (t, 1H, J=2.7, CHO); 6.12 and 6.02 (2d, 2H, J=16.4, $C_7$—H+$C_8$—H); 5.20 and 5.07 (2 bs, 2H, $C_9$—H); 3.37 (d, 2H, J=2.7, $C_{10}$—H); 1.97 (m, 2H, $C_3$—H); 1.64 (s, 3H, $C_2$-$CH_3$); 1.56 (m, 2H, $C_4$—H); 1.44 m, 2H, $C_5$—H); 0.96 (s, 6H, $C_6$—$CH_3$). $^{13}$C NMR ($CDCl_3$); 199.5 ($C_{11}$); 137.6 (C-1); 136.8 ($C_2$); 133.9 and 129.1 ($C_7$+$C_8$); 129.3 ($C_9$); 118.4 ($CH_2$-$C_9$); 44.3 ($C_{10}$); 39.1 ($C_5$); 33.8 ($C_6$); 32.5 ($C_3$); 28.5 ($C_2$-$CH_3$); 21.2 ($C_6$—$CH_3$); 18.9 ($C_4$).

EXAMPLE 2

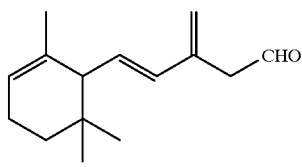

Preparation of compound of formula

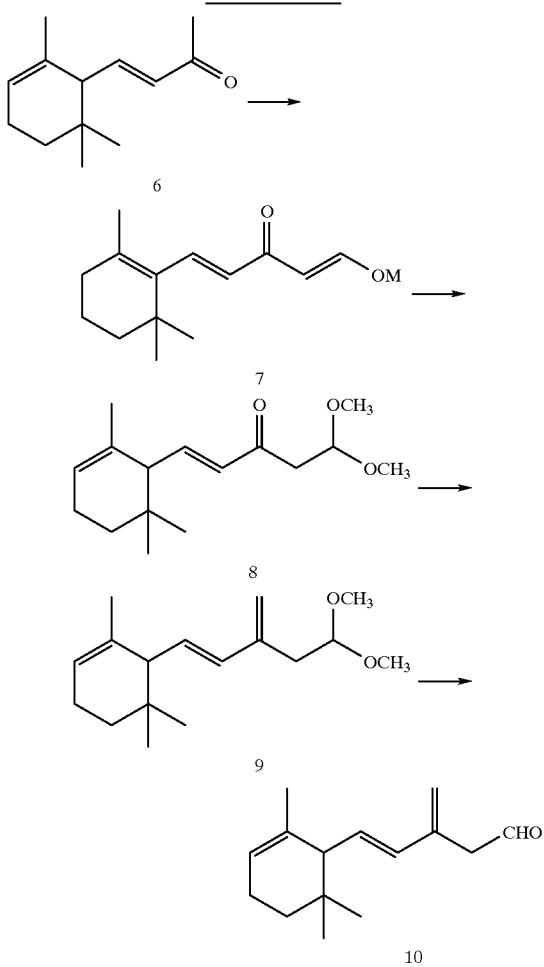

Synthetic scheme

The operating conditions are identical to those of Example 1. The characteristics of the compounds 7, 8, 9 and 10 obtained are given below. compound No. 7 (sodium salt) IR (KBr) 2868, 2920, 2868, 1657, 1600, 1500, 1450, 1360, 1220, 990, 770, 545.

compound No. 7 IR 2967, 2921, 2854, 1624, 1585, 1446, 1295, 1216, 986, 775, 551. $^1$H NMR (CDCl$_3$) : 0.86 and 0.78 (2s, 6H, C$_6$—CH$_3$); 1.3 (m, 2H, C$_5$—H); 1.57 (s, 3H, C$_2$-CH$_3$); 1.96 (m, 2H, C$_4$—H); 2.23 (d, 1H, J=5 , C$_1$—H); 5.42 (m, 1H, C$_3$—H); 5.50 (d, 1H, J=3.5, C$_{10}$—H); 5.82 (d, 1H, J=16, C$_8$—H); 6.62 (dd, 1H, J=16, J=5, C$_7$—H); 8.41 (d, 1H, J=3.5, C$_{11}$—H).

compound No. 8 IR (Film v cm$^{-1}$) 2970, 2920, 2875, 1670, 1625, 1450, 1375, 1130, 1088, 992. $^1$H NMR (CDCl$_3$): 0.89 and 0.81 (2s, 6H, C$_6$—CH$_3$); 1.30 (m, 2H, C$_5$—H); 1.50 (s, 3H, C$_2$-CH$_3$); 2.00 (m, 2H, C$_4$—H); 2.28 (d, 1H, J=9, C$_1$—H); 2.80 (d, 2H, J=5, C$_1$—H); 3.30 (8, 6H, OCH$_3$); 4.77 (t, 1H, J=5 C$_{11}$—H); 5.40 (m, 1H, C$_3$—H); 6.00 (d, 1H, J=16, C$_8$—H); 6.62 (dd, 1H, J=16, J'=9, C$_7$—H). $^{13}$C NMR (CDCl$_3$): 207.1 (C$_9$); 183.9 (C$_1$); 149.3 (C$_7$); 131.8 (C$_8$); 122.7 (C$_3$); 102.1 (C$_{11}$); 54.8 (C$_1$); 54.1 (OCH$_3$); 43.9 (C$_{10}$); 32.5 (C$_6$); 31.2 (C$_5$); 27.7 (C$_2$-CH$_3$); 26.6 (C$_6$—CH$_3$); 23.0 (C$_4$); 19 .7 (C$_6$—CH$_3$).

compound No. 9 IR (film): 2930, 1602, 1122, 1068, 971, 888. $^1$H NMR (CDCl$_3$): 6.02 (d, 1H, J=16, C$_8$—H); 5.51 (dd, 1H, J=16, J'=9.5, C$_7$—H); 5.39 (m, 1H, C$_3$—H); 4.98 (2s, 2H, C$_9$—CH$_2$); 4.50 (t, 1H, J=5.5, C$_{11}$ ); 3.30 (s, 6H, OCH$_3$); 2.49 (d, 2H, J=5.5, C$_{10}$—H); 2.12 (d, 1H, J=9.5, C$_1$—H); 1.98 (m, 2H, C$_4$—H); 1.55 (s, 3H, C$_2$-CH$_3$); 1.26 (m, 2H, C$_5$—H); 0.85 and 0.83 (2s, 6H, C$_6$—CH$_3$). $^{13}$C NMR (CDCl$_3$): 140.8 (C$_2$); 132.8 (C$_7$); 131.8 (C$_8$); 128.0 (C$_9$); 120.3 (C$_3$); 115.5 (CH$_2$-C$_9$); 103.1 (C$_{11}$); 54.3 (OCH$_3$); 52.6 (C$_1$); 35.8 (C$_{10}$); 32.0 (C$_6$); 31.4 (C$_5$); 26.6 (C$_2$-CH$_3$); 22.6 (C$_4$); 19.2 (C$_6$—CH$_3$).

compound No. 10 IR (film): 2930, 2715, 1727, 1603. $^1$H NMR (CDCl$_3$): 9.60 (t, 1H, J=2.7, C$_{11}$—H); 6.13 (d, 1H, J=16, C$_8$—H); 5.42 (dd, 1H, J=16, J'=5, C$_7$—H); 5.35 (bs, 1H, C$_3$—H); 5.18 and 5.03 (2s, 2H, C$_9$—CH$_2$); 3.21 (d, 2H, J=2.7, C$_{10}$—H); 2.14 (d, 1H, J=5, C$_1$—H); 1.99 (m, 2H, C$_4$—H); 1.53 (s, 3H, C$_2$-CH$_3$); 1.27 (m, 2H, C$_5$—H); 0.87 and 0.76 (2s, 6H, C$_6$—CH$_3$). $^{13}$C NMR (CDCl$_3$): 220.3 (C$_{11}$); 137.6 (C$_2$); 133.7 (C$_7$); 133.9 and 132.6 (C$_8$); 121.7 (C$_9$); 121.5 (C$_3$); 118.4 (CH$_2$-C$_9$); 54.7 (C$_1$); 48.0 (C$_{10}$); 32.5 (C$_6$); 31.8 (C$_5$); 27.5 (C$_2$-CH$_3$); 27.1 (C$_6$—CH$_3$); 23.0 (C$_4$); 22 .8 (C$_6$CH$_3$)

EXAMPLE 3

Preparation of compound No. 12

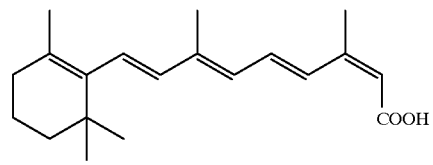

Synthetic scheme

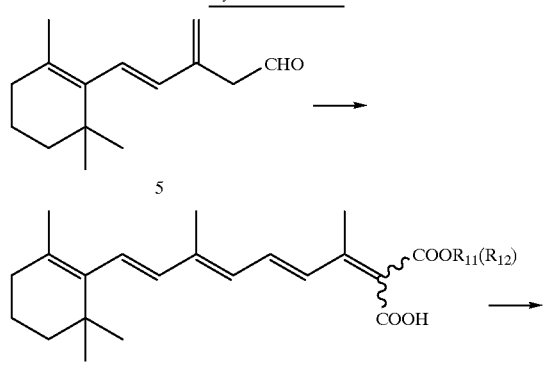

15
-continued

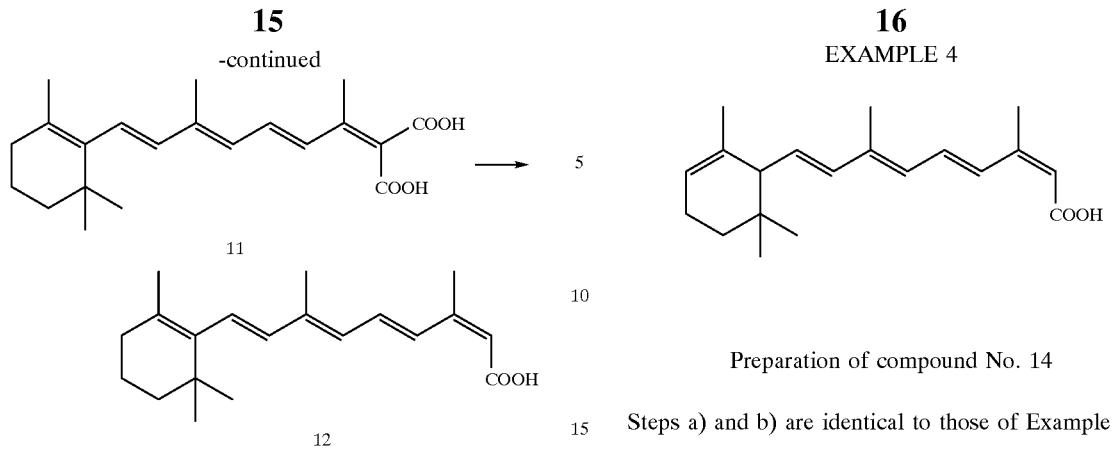

a) Preparation of compound No. 11

1.3 g of aldehyde are added slowly, under argon and between 0 and 5° C., to a solution of 1.5 g of dimethyl isopropylidenemalonate in 8 ml of Triton B (40% in methanol). After 2 h at room temperature, the solution is acidified with ice-cold 10% HCl solution and is extracted with ether. The ester acid is extracted with aqueous 5% sodium hydroxide solution and then released from its sodium salt with 10% HCl solution. The crude product (yield =95%) is saponified with 0.75 N sodium hydroxide solution (60% $H_2O$, 40% MeOH), for 1 h 30 at boiling (yield =100%). Yellow crystals, m.p.=198° C.

b) Preparation of compound No. 12

1.5 g of diacid are heated for 2 h at boiling in 50 ml of 2,6-dimethylpyridine. After distillation of the base under reduced pressure, the mixture is cooled to about 0° C. and is acidified with 10% HCl solution. The acid is extracted with ether. Yield =100%. The acid crystallizes from ether.

The characteristics of compounds 11 and 12 are as follows:

compound No. 11 (derivative of aldehyde 5) IR (KBr): 2927, 1676, 1611, 1571, 1455, 1255, 979, 722. $^1$H NMR ($CDCl_3$); 7.17 (m, 1H, $C_{11}$—H); 6.95 (d, 1H, J=16, $C_{12}$) ; 6.28 (m, 2H, $C_7+C_{10}$—H); 6.18 (d, 1H, J=16, $C_8$); 2.13 (B, 3H, $C_{13}$—$CH_3$); 2.02 (m, 2H, $C_3$—H); 1.98 (s, 3H, $C_9$—$CH_3$); 1.58 (s, 3H, $C_9$—$CH_3$); 1.50 (m, 2H, $C_4$—H); 1.46 (m, 2H, $C_5$—H); 1.00 (s, 6H, $C_6$—$CH_3$). $^{13}$C NMR ($CDCl_3$): 167.7 and 167.3 (C-15+$C_{15}$—COOH); 146.3 (C-14); 143.9 (C-13); 141.1 (C-9); 137.7 (C-1); 137.3 (C-12); 133.5 (C-7); 130.6 (C-8); 130.4 (C-11); 128.8 (C-10); 126.7 (C-2); 34.3 (C-6); 34.1 (C-5); 29.2 ($C_2$-$CH_3$); 21.9 ($C_6$—$CH_3$); 19.2 (C-4); 16.0 ($C_{13}$—$CH_3$); 13.1 ($C_{13}$—$CH_3$)

compound No. 12 (13 Z, derivative of aldehyde 5) IR (KBr): 2960, 2921, 2861, 1683, 1591, 1387, 1249, 972 $^1$H NMR ($CDCl_3$): 7.72 (d, 1H, J=16, $C_{12}$—H); 7.02 (m, 1H, $C_{11}$—H); 6.27, 6.25, 6.17 (m, 3H, $C_7+C_8+C_{10}$—H); 5.64 (bs, 1H, $C_{14}$—H); 2.08 (s, 3H, $C_{13}$—$CH_3$); 2.00 (m, 2H, $C_4$—H); 1.98 (s, 3H, $C_9$—$CH_3$); 1.69 (s, 3H, $C_2$-$CH_3$); 1.59 (m, 2H, $C_5$—H); 1.46 (m, 2H, $C_3$—H); 1.00 (s, 6H, $C_6$—$CH_3$).

16
EXAMPLE 4

Preparation of compound No. 14

Steps a) and b) are identical to those of Example 3.

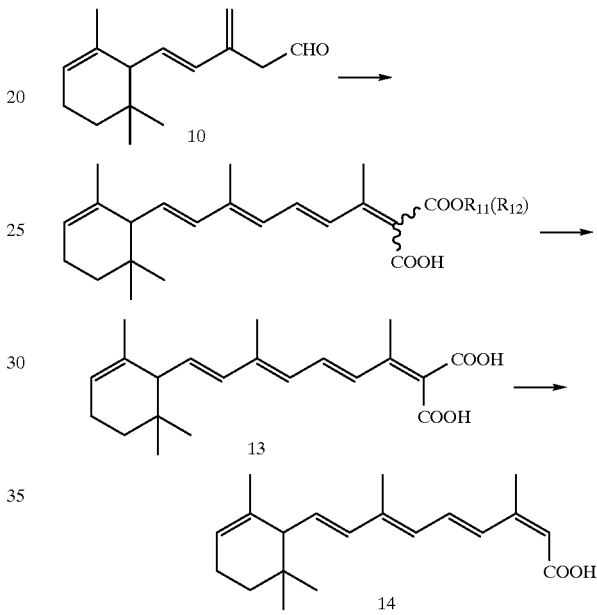

The characteristics of compounds 13 and 14 are as follows:

compound No. 13 (derivative of aldehyde 10) IR (KBr): 2940, 2919, 2604, 1710, 1575, 1251, 970, 722. $^1$H NMR ($CDCl_3$): 7.05 (m, 2H, $C_{11}+C_8$—H; 6.12 (d, 1H, J=10, $C_{10}$—H); 6.04 (d, 1H, J=16, $C_{12}$—H); 5.60 (dd, 1H, J=16, J'=9 $C_7$—H); 5.34, (m, 1H, $C_3$—H); 2.18 (s, 3H, $C_9$—$CH_3$); 2.10 (d, 1H, J=9, $C_1$—H); 1.90 (m, 2H, $C_4$—H); 1.87 (8, 3H, $C_2$-$CH_3$); 1.50 (s, 3H, $C_{13}$—$CH_3$); 1.20 (m, 2H, $C_5$—H); 0.85 and 0.70 (2s, 6H, $C_6$—$CH_3$). $^{13}$C NMR ($CDCl_3$); 185.8 (CO); 168.8 ($C_{14}$); 168.3 ($C_1$); 143.0 ($C_{13}$); 134.0 ($C_9$); 135.7, 133.7, 133.6, 133.0 ($C_7+C_8+C_{10}+C_{11}$); 129.5 ($C_{12}$); 121.0 ($C_3$); 54.8 ($C_1$); 32.5 ($C_6$); 31.6 ($C_4$); 27.7 ($C_2$-$CH_3$); 26.9 ($C_6$—$CH_3$); 16.2 ($C_6CH_3$); 13.3 ($C_6$—$CH_3$).

compound No. 14 (13 Z derivative of aldehyde 10) IR (KBr): 2934, 1683, 1604, 1572, 1249, 972 $^1$H NMR ($CDCl_3$): 7.67 (d, 1H, J=16, $C_{12}$); 6.80 (m, 1H, $C_{11}$—H); 5.90 (m, 2H, $C_8+C_{10}$); 5.70 (m, 1H, $C_3$—H); 5.40 (dd, 1H, $C_7$—H); 2.28 (d, 1H, $C_1$—H); 2.0 (s, 3H, $C_2$-$CH_3$); 1.90 (s, 3H, $C_9$—$CH_3$); 1.85 (s, 3H, $C_{13}$—$CH_3$); 1.50 (m, 2H, $C_4$—H); 1.30 (m, 2H, $C_5$—H); 0.9 and 0.8 (2s, 6H, $C_6$—$CH_3$).

We claim:
1. A β-methylene aldehyde of formula

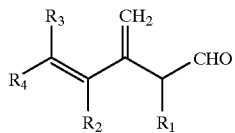

in which:
- $R_1$ and $R_2$, which may be identical or different, are a hydrogen atom or substituted carbocyclic hydrocarbon radicals,
- $R_3$ and $R_4$, which may be identical or different, are a hydrogen atom or substituted carbocyclic hydrocarbon radicals, it not being possible for $R_3$ and $R_4$ simultaneously to be a hydrogen atom.

2. The β-methylene aldehyde as claimed in claim 1, in which, in the case of the carbocyclic, groups, the substituents (Z) are identical or different and are halogen atoms, alkyl, haloalkyl, hydroxyl, alkoxy, haloalkoxy, thiol, alkylthio, haloalkylthio, alkylsulfinyl, haloalkylsulfinyl, alkylsulfonyl, haloalkylsulfonyl, alkoxycarbonyl, haloalkoxycarbonyl, alkylcarbonyloxy, haloalkylcarbonyloxy, alkylcarbonyl, haloalkylcarbonyl, amino, alkylamino, haloalkylamino, dialkylamino, dihaloalkylamino, alkylhaloalkylamino, nitro, cyano, oxo, optionally cyclic acetal, imine, oxime or carboxyamido radicals or a residue —$S(O)_m$—R in which R is an amino, alkylamino or dialkylamino group and m =0, 1 or 2.

3. The β-methylene aldehyde as claimed in claim 1, in which, when the carboacyclic, carbocyclic or heterocyclic hydrocarbon radicals are substituted, the number of substituents is between 1 and 6.

4. The β-methylene aldehyde as claimed in claim 1, in which $R_4$ is a saturated or mono- or di-unsaturated aromatic ring containing 6 carbon atoms, optionally substituted with $C_{1-C4}$ alkyl, hydroxyl or $C_1$–$C_4$-alkoxy radicals or an oxo function and $R_3$ is a hydrogen atom.

5. The β-methylene aldehyde as claimed in claim 1, in which $R_2$ is a hydrogen atom.

6. The β-methylene aldehyde as claimed in claim 1, in which $R_1$ is a hydrogen atom.

7. The β-methylene aldehyde as claimed in claim 1, in which the unit:

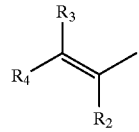

is a terminal residue of a compound selected from retinoids, carotenoids or the respective structural analogs thereof.

8. The β-methylene aldehyde as claimed in claim 7 in which the moiety

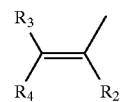

is a terminal residue of a compound selected from the following compounds:

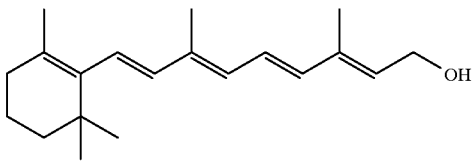

Retinol (vitamin A)

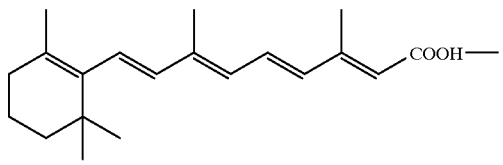

Retinoic acid

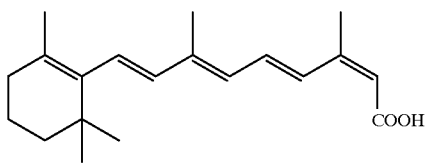

13Z-retionic acid

-continued
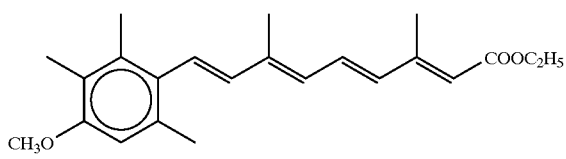
Etretinate
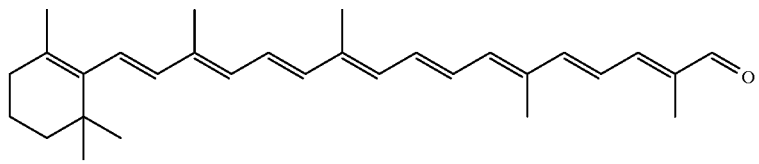
β-Apo-8'-carotenal
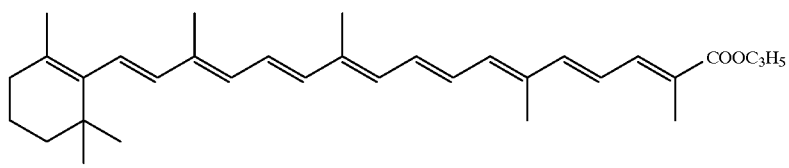
E–β-apo-8'-carotenoic acid
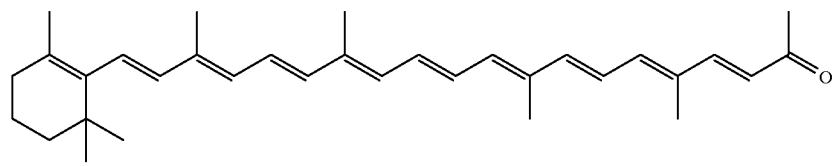
Citranaxanthine
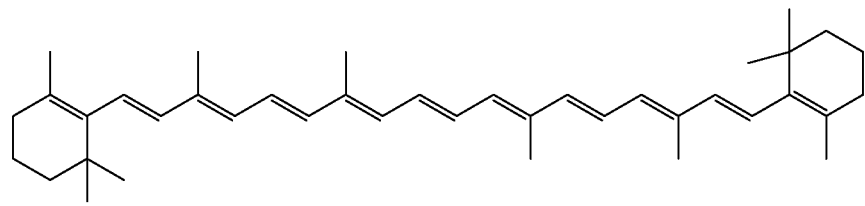
β-carotene
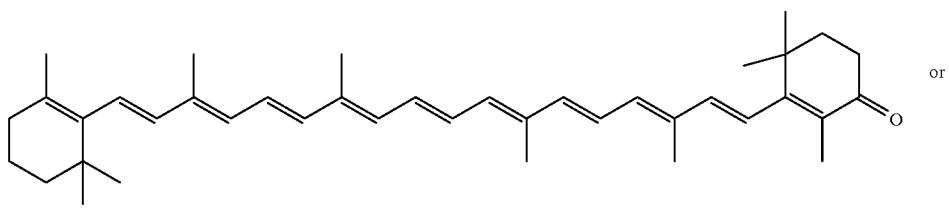
or
Cantaxanthine -continued Astaxanthine 9. The β-methylene aldehyde as claimed in claim 8, in which $R_4$ is an optionally substituted 2,6 6-trimethyl-cyclohexenyl radical.

10. The β-methylene aldehyde as claimed in claim 9, in which $R_4$ corresponds to the formula:

α

β

11. A process for the preparation of compounds of interest, wherein a compound of formula (I) as claimed in claim 1 is reacted with a compound having a hydrogen capable of being activated, of formula II $R_1$ and $R_2$ which may be identical or different, are a hydrogen atom or optionally substituted carboacyclic, carbocyclic or heterocyclic hydrocarbon radicals.

$R_3$ and $R_4$, which may be identical or different, are a hydrogen atom or optionally substituted carboacyclic, carbocyclic or heterocyclic hydrocarbon radicals, it not being possible for $R_3$ and $R_4$ simultaneously to be a hydrogen atom, and $R_5$ and $R_6$, which may be identical or different, are a hydrogen atom, a lower alkyl radical or an electron-withdrawing group on condition that one of the radicals is an electron-withdrawing group, or $R_5$ is a hydrogen atom and $R_6$ is a group $—CR_7=C(R_8)_2$ where $R_7$ is a hydrogen atom or a lower alkyl radical and $R_8$ is an electron-withdrawing group, in the presence of an agent for activating said hydrogen, and then recovering a compound of formula III and in optionally converting said compound of formula III.

12. The preparation process as claimed in claim 11, wherein the compound of formula II is involved in the skeleton of a compound selected from retinoids, carotenoids or the respective structural analogs thereof.

13. The preparation process as claimed in claim 12, wherein the compound of formula II corresponds to the formula:

in which:

$R_9$ is a hydrogen atom or an optionally substituted alkyl radical, $R_{10}$ is a hydrogen atom or an alkyl radical, $R_{11}$ and $R_{12}$ are such that the ester functions $COOR_{11}$ or $COOR_{12}$ can be hydrolyzed into acid functions and the compound of formula III corresponds to the formula:

14. The preparation process as claimed in claim 13, wherein the compound of formula II is an isopropylidene-malonic acid ester.

15. The preparation process as claimed in claim 11, wherein the agent which activates the hydrogen of the methylene or of the methyl is quaternary ammonium hydroxides or alkaline amides.

16. The process as claimed in claim 11, wherein the I/II molar ratios are between 0.2 and 2.

* * * * *